(12) United States Patent
Hayashi et al.

(10) Patent No.: US 9,316,589 B2
(45) Date of Patent: Apr. 19, 2016

(54) METHOD FOR EVALUATING OXIDE SEMICONDUCTOR THIN FILM, AND METHOD FOR QUALITY CONTROL OF OXIDE SEMICONDUCTOR THIN FILM

(71) Applicant: Kobe Steel, Ltd., Hyogo (JP)

(72) Inventors: Kazushi Hayashi, Kobe (JP); Toshihiro Kugimiya, Kobe (JP); Tomoya Kishi, Kobe (JP); Aya Miki, Kobe (JP)

(73) Assignee: Kobe Steel, Ltd., Hyogo (JP)

( * ) Notice: Subject to any disclaimer, the term of this patent is extended or adjusted under 35 U.S.C. 154(b) by 0 days.

(21) Appl. No.: 14/760,023

(22) PCT Filed: Sep. 4, 2013

(86) PCT No.: PCT/JP2013/073848
§ 371 (c)(1),
(2) Date: Jul. 9, 2015

(87) PCT Pub. No.: WO2014/112153
PCT Pub. Date: Jul. 24, 2014

(65) Prior Publication Data
US 2015/0355095 A1 Dec. 10, 2015

(30) Foreign Application Priority Data

Jan. 15, 2013 (JP) .................. 2013-004708
Mar. 18, 2013 (JP) .................. 2013-055795

(51) Int. Cl.
*F21V 9/16* (2006.01)
*G01J 1/58* (2006.01)
(Continued)

(52) U.S. Cl.
CPC ............ *G01N 21/6489* (2013.01); *H01L 22/12* (2013.01); *H01L 29/24* (2013.01); *H01L 29/66969* (2013.01); *H01L 29/78693* (2013.01)

(58) Field of Classification Search
CPC .................................................. G01N 21/6489
USPC ............................................. 250/459.1, 216
See application file for complete search history.

(56) References Cited

U.S. PATENT DOCUMENTS

2006/0272573 A1* 12/2006 Hachigo ............ G01N 21/9501
117/88
2012/0203473 A1 8/2012 Hayashi et al.
2013/0153778 A1 6/2013 Sakoda et al.

FOREIGN PATENT DOCUMENTS

JP 2006-339605 A 12/2006
JP 2008-191123 A 8/2008
(Continued)

OTHER PUBLICATIONS

International Search Report; PCT/JP2013/073848; Dec. 3, 2013.
(Continued)

*Primary Examiner* — Casey Bryant
*Assistant Examiner* — Meenakshi Sahu
(74) *Attorney, Agent, or Firm* — Studebaker & Brackett PC (57) ABSTRACT

This method for evaluating an oxide semiconductor thin film includes evaluating the stress stability of an oxide semiconductor thin film on the basis of the light emission intensity of luminescent light excited when radiating an electron beam or excitation light at a sample at which the oxide semiconductor thin film is formed. The stress stability of the oxide semiconductor thin film is evaluated on the basis of the light emission intensity (L1) observed in the range of 1.6-1.9 eV of the luminescent light excited from the oxide semiconductor thin film.

12 Claims, 5 Drawing Sheets

(51) Int. Cl.
- *G01T 1/10* (2006.01)
- *G21H 3/02* (2006.01)
- *G21K 5/00* (2006.01)
- *H01J 65/06* (2006.01)
- *G01N 21/64* (2006.01)
- *H01L 21/66* (2006.01)
- *H01L 29/24* (2006.01)
- *H01L 29/66* (2006.01)
- *H01L 29/786* (2006.01)

(56) References Cited

FOREIGN PATENT DOCUMENTS

| | | |
|---|---|---|
| JP | 2009-164393 A | 7/2009 |
| JP | 2012-019207 A | 1/2012 |
| JP | 2012-033857 A | 2/2012 |
| JP | 2014-019931 A | 2/2014 |
| WO | 2014/109343 A1 | 7/2014 |
| WO | 2015/037596 A1 | 3/2015 |

OTHER PUBLICATIONS

Written Opinion of the International Searching Authority; PCT/JP2013/073848; Dec. 3, 2013.

Tomoya Kishi et al., "Evaluation of electronic and optical properties in oxide semiconductors (I)—Process dependences of electronic states examined by cathodoluminescence", Japan Society of Applied Physics and Related Societies, Mar. 2012, p. 21-078(17p-E4-11).

Myungkwan Ryu et al., "High mobility zinc oxynitride-TFT with operation stability under light-illuminated bias-stress conditions for large area and high resolution display applications", Tech.Dig.Int. Electron Devices Meet, 2012, p. 112-114.

Keiko Inoue et al., "Characterization of a IGZO Films by Raman Spectroscopy and Cathodoluminescence Spectroscopy", Japan Society of Applied Physics and Related Societies, 2011, p. 21-006(24a-BS-6).

\* cited by examiner

METHOD FOR EVALUATING OXIDE SEMICONDUCTOR THIN FILM, AND METHOD FOR QUALITY CONTROL OF OXIDE SEMICONDUCTOR THIN FILM

FIELD OF TECHNOLOGY

The present invention relates to an evaluation method for an oxide semiconductor thin film. Specifically, the present invention relates to a technology for judging and evaluating stress stability of an oxide semiconductor thin film in a non-destructive and contactless manner, and a quality control method for an oxide semiconductor thin film.

BACKGROUND ART

In addition to widely-used amorphous silicon (a-Si), amorphous (non-crystalline) oxides comprising for example at least one kind of indium (In), gallium (Ga), zinc (Zn), tin (Sn) and so on are recently used for a semiconductor layer of a thin film transistor (TFT). Such an oxide semiconductor thin film comprising the oxide used for a semiconductor layer in a TFT has excellent semiconducting properties including high field-effect (carrier) mobility. In addition, the oxide semiconductor thin film has a wide optical band gap and film formability at low temperatures, which makes the formation on a plastic substrate or a film substrate possible.

However, as compared with a case of using a-Si, an oxide semiconductor thin film is liable to vary in terms of electrical characteristics and has a problem of low reliability when used for a display device such as a liquid crystal display or an organic EL display. It has been pointed out for example in Patent Document 1 that if there is a variation (shift) of threshold voltage (which is a gate voltage necessary to turn a transistor to the on-state) in a semiconductor element such as a transistor before and after light irradiation or bias-thermal stress test (BT test), the on/off state may not be controlled in a normal manner, resulting in significant deterioration of the reliability of the transistor. For an oxide semiconductor thin film, it is desired the threshold voltage ($V_{th}$) does not shift in I-V characteristics (drain current-gate voltage characteristics: variation in drain current with respect to change in gate voltage), that is excellent stress stability, when an oxide semiconductor thin film is subjected to the stress test in which a semiconductor element such as a transistor is subjected to being kept under light irradiation or continuous application of gate bias.

On the other hand, it is thus essential from the point of view to improving the productivity to evaluate properties of deposited oxide semiconductor thin films, to feedback the results of the evaluation, to develop a material for a semiconductor device or to adjust manufacturing conditions by optimizing a process, and to control film quality in the manufacturing process of the display devices. Desired for an oxide semiconductor thin film is a technology to accurately measure or predict and evaluate variation of the electrical property (amount of threshold voltage shift $\Delta V_{th}$) induced by the stress in a semiconductor device.

In a conventional evaluation method for evaluation of electrical properties of an oxide semiconductor thin film, the properties such as mobility and threshold voltage are measured in an actual TFT or a device simulating the TFT for which a gate insulator film or a passivation insulator film and contact electrodes are formed on the semiconductor thin film. It takes, however, enormous amount of time and cost to form contact electrodes in such contacting type evaluation methods that require actual fabrication of the devices. Forming the electrodes is also liable to induce additional defects in the oxide semiconductor thin film. In addition, it requires time to form the electrodes in the devices. It has thus been required from the point of view to improving fabrication yield to establish a contactless-type evaluation method in which formation of contact electrodes is not necessary.

In view of these circumstances, evaluation methods by microwave photo conductivity decay method (μ-PCD method) utilizing laser and microwave have been proposed as a method for evaluating the characteristics of a semiconductor thin film in a non-contact manner (Patent Document 2 and Patent Document 3).

Among these, the method according to Patent Document 2 has been proposed to evaluate the crystal quality of a crystalline semiconductor thin film such as polycrystal silicon. A specimen comprising the crystalline semiconductor thin film is irradiated with a laser. The crystal quality of the semiconductor thin film is evaluated by measuring the change in reflectance of the microwave which depends on the excess carriers generated by the laser irradiation.

Further, the technology of Patent Document 2 has been modified in Patent Document 3 so that irradiation conditions of excitation light is properly set for an oxide semiconductor thin film for the purpose of evaluating characteristics of the oxide semiconductor thin film which is amorphous. Specifically, Patent Document 3 discloses (I) a method comprising irradiating both excitation light and microwave radiation to a specimen on which an oxide semiconductor thin film is formed, measuring the maximum value (peak value) of reflected wave of the microwave radiation, which varies with the irradiation of the excitation light, from the oxide semiconductor thin film, then stopping the irradiation of the excitation light, and thereafter measuring a variation in the reflectance of the microwave radiation reflected by the oxide semiconductor thin film after the stopping, and evaluating mobility of the oxide semiconductor thin film by calculating lifetime value (1/e of change in the reflectance) from the measured value; and (II) a method of evaluating mobility of an oxide semiconductor thin film by irradiating both excitation light and microwave radiation to a specimen on which an oxide semiconductor thin film is formed, and measuring the maximum value (peak value) of reflected wave of the microwave radiation, which varies with the irradiation of the excitation light, from the oxide semiconductor thin film.

PRIOR ART DOCUMENTS

Patent Document

Patent Document 1: Japanese Patent Laid-open Publication No. 2012-19207
Patent Document 2: Japanese Patent Laid-open Publication No. 2008-191123
Patent Document 3: Japanese Patent Laid-open Publication No. 2012-33857

SUMMARY OF THE INVENTION

Problems to be Solved by the Invention

The technology of Patent Document 3 is, however, a method for evaluating mobility of an oxide semiconductor thin film using a μ-PCD method in a contactless manner. It is not a method to evaluate the stress stability which is of particular problem in an oxide semiconductor thin film.

In addition to the above, as a method for evaluating the deterioration (change in the electrical characteristics) of a semiconductor element caused by a stress, there is, for example, NBTI (negative bias temperature instability) test. The NBTI test is a test to evaluate the changes in the electrical characteristics of a transistor by applying a negative bias to a gate terminal of the transistor. It is a contact type evaluation test which requires preparation of an actual TFT or a device simulating it.

A method for evaluating stress stability of an oxide semiconductor thin film in a non-contact manner has been strongly desired, accordingly.

The present invention has been made in view of the circumstances described above, and an object of the present invention is to provide a method to easily evaluate (predict or estimate) stress stability (amount of threshold voltage shift $\Delta V_{th}$ caused by the stress) of an oxide semiconductor thin film in a non-destructive and contactless manner; preferably a method to more accurately evaluate (predict or estimate) the stress stability ($\Delta V_{th}$); and a quality control method for an oxide semiconductor.

Means for Solving the Problems

The method for evaluating an oxide semiconductor thin film according to the present invention which can solve the above-mentioned problems is comprising evaluating the stress stability of an oxide semiconductor thin film on the basis of the light emission intensity of luminescent light excited when radiating an electron beam or excitation light at a sample on which the oxide semiconductor thin film is formed. The stress stability of the oxide semiconductor thin film is evaluated on the basis of the light emission intensity (L1) observed in the range of 1.6 to 1.9 eV of the luminescent light emitted from the oxide semiconductor thin film.

In a preferred embodiment of the present invention, the stress stability of the oxide semiconductor thin film is evaluated on the basis of peak intensity (P1) observed in the range of 1.6-1.9 eV.

In a preferred embodiment of the present invention, the stress stability of the oxide semiconductor thin film is evaluated on the basis of an intensity ratio of energies corresponding to each of the luminescent light generated across a plurality of energy levels in the oxide semiconductor thin film from which the luminescent light is emitted.

In a preferred embodiment of the present invention, the intensity ratio (L1/L2) is a ratio of a light emission intensity (L1) observed in a range of 1.6 to 1.9 eV to a light emission intensity (L2) observed in a range of 3.0 to 3.2 eV corresponding to the band-to-band transition.

In a preferred embodiment of the present invention, the intensity ratio (P1/P2) is a ratio of a peak intensity (P1) observed in a range of 1.6 to 1.9 eV to a peak intensity (P2) observed in a range of 3.0 to 3.2 eV corresponding to the band-to-band transition.

In a preferred embodiment of the present invention, the oxide semiconductor thin film comprises one or more kinds of element selected from a group consisting of In, Ga, Zn, and Sn.

The present invention also provides a quality control method for an oxide semiconductor thin film in which the evaluation method is applied to any of manufacturing processes of the semiconductor after forming the oxide semiconductor thin film on a substrate.

The present invention provides a quality control method for an oxide semiconductor thin film comprising one or more kinds of element selected from a group consisting of In, Ga, Zn, and Sn used as a semiconductor layer of a thin film transistor. It is a method comprising (A) radiating an electron beam to the oxide semiconductor thin film and measuring a fluorescence spectrum induced by the irradiation, and (B) evaluating the thin film on the basis of the fluorescence spectrum. The method is characterized in that it uses intensity ratio of each energy corresponding to each luminescence generated between a plurality of energy levels as the standard of evaluation in the (B) process.

The quality control method performs a so-called cathodoluminescence measurement for the oxide semiconductor thin film ((A) process), and an evaluation of the oxide semiconductor thin film using the intensity ratio of the fluorescence spectra ((B) process). It is possible to perform the measurement and evaluation at each manufacturing process even before completion of fabricating a transistor.

It is preferred that the intensity of the energy is a maximum value of the fluorescence spectrum. It is possible to perform the evaluation and control in an efficient manner by using the maximum value when determining the intensity.

An intensity ratio $I_m/I_1$ is preferably used in the intensity of the energy wherein $I_1$ is intensity of an energy $X_1$ corresponding to fluorescence generated between the conduction band and the valence band, and $I_2, I_3, \ldots I_m$ are intensities of one or more of the energy $X_2, X_3, \ldots X_m$ corresponding to fluorescence generated between the other energy levels (where m is an integer of 2 or larger).

The intensity ratio $I_m/I_1$ based on the intensity of the energy corresponding to the bandgap between the conduction band and the valence band is correlated with status of each of the energy levels formed in the oxide semiconductor thin film. It is thus possible to perform an evaluation with higher accuracy by using this intensity ratio.

The (A) process and (B) process are applied to manufacturing a thin film transistor comprising;
(X) a process of forming an oxide semiconductor thin film,
(Y) a process of annealing the oxide semiconductor thin film, and
(Z) a process of forming a passivation film on a surface of the oxide semiconductor thin film.
The (A) and (B) processes are to be performed after each of the (X), (Y) and (Z) processes.

In the production of the TFTs, conditions of depositing an oxide semiconductor thin film and its heat treatment as well as deposition of a passivation film on a surface of the oxide semiconductor thin film have a large influence on the quality of the oxide semiconductor thin film. It becomes thus possible to execute quality control in an efficient manner in the course of the manufacturing process by performing the measurement and evaluation after each of the processes (X) to (Z).

When the oxide semiconductor thin film includes In, Ga, Zn, and O, and
the fluorescent energy $X_1$ is 3.3 eV±0.2 eV,
the fluorescent energy $X_2$ is 2.5 eV±0.3 eV, and
the fluorescent energy $X_3$ is 1.9 eV±0.3 eV, the criteria may be set to;
an intensity ratio $I_2/I_1$ is equal to or larger than 2.0 and equal to or smaller than 15.0, and/or an intensity ratio $I_3/I_1$ is equal to or larger than 3.0 and equal to or smaller than 30.0, after the (X) process,
an intensity ratio $I_2/I_1$ is equal to or larger than 5.0 and equal to or smaller than 30.0, and/or an intensity ratio $I_3/I_1$ is equal to or larger than 15.0 and equal to or smaller than 80.0, after the (Y) process, and
an intensity ratio $I_2/I_1$ is equal to or larger than 6.0 and equal to or smaller than 20.0, and/or an intensity ratio $I_3/I_1$ is equal to or larger than 25.0 and equal to or smaller than 70.0, after the (Z) process.

In the production of IGZO thin film, it is possible to perform a better quality control by employing the above-mentioned specific criteria for each process.

The oxide semiconductor thin film may be preferably formed on the surface of the gate insulator film in (A) process. In addition, a passivation film may be preferably formed on a surface of the oxide semiconductor thin film in (A) process. Quality control in each production process is facilitated by performing the measurement and evaluation for a thin film of such deposition states.

Here "energy level" means a value of the energy that can be taken by electrons and includes, not only a defect level, an acceptor level, a donor level and the like, but also the valence and conduction bands.

Effects of the Invention

The stress stability ($\Delta V_{th}$) of an oxide semiconductor thin film can be easily evaluated (predicted or estimated) in a non-destructive and contactless manner by using emission intensity of excited luminescence light (preferably peak intensity) as the present invention.

The stress stability ($\Delta V_{th}$) of an oxide semiconductor thin film can be evaluated (predicted or estimated) with higher accuracy by using preferably, the intensity ratio (preferably the peak intensity ratio) of energy corresponding to each luminescent light generated between a plurality of energy levels.

By using the evaluation method according to the present invention, stress stability of oxide semiconductor thin films having various compositions and concentrations can be easily evaluated in a short period of time at low cost in a material development stage of an oxide semiconductor thin film. Further, by applying the evaluation method according to the present invention to a production line for a liquid crystal display device or the like, electrical properties of an oxide semiconductor thin film can be evaluated in-line in a short period of time in a contactless manner. The productivity such as production yield can be improved and quality control of an oxide semiconductor thin film can be appropriately executed.

MODE FOR CARRYING OUT THE INVENTION

First feature of the present invention lies in using the emission intensity of luminescence excited by irradiation of excitation light or an electron beam to a specimen comprising an oxide semiconductor thin film as an index to conveniently evaluate (predict or estimate) the stress stability of the oxide semiconductor thin film in a non-destructive and contactless manner. Among the luminescence, the emission intensity L1 (more preferably a peak intensity P1) observed in the range of 1.6 to 1.9 eV is preferably used as the index of evaluation of the stress stability. Comparative evaluation (for instance, judgment of acceptance/rejection) of the stress stability of the oxide semiconductor thin film can be basically executed by using the index. As described below in Example 1, a peak intensity P1 observed in the above-mentioned range and the stress stability of the oxide semiconductor thin film ($\Delta V_{th}$) have a generally good correlation as described below in Example 1, and as P1 becomes larger, $\Delta V_{th}$ tends to increase (that is, the stress stability is deteriorated). P1 is thus a useful index to simply and qualitatively evaluate the stress stability of the oxide semiconductor thin film.

Second feature of the present invention lies in using the intensity ratio of energies corresponding to each luminescence generated across multiple energy levels in an oxide semiconductor thin film as an index to evaluate the stress stability of the oxide semiconductor thin film with higher accuracy. For the intensity ratio, an emission intensity ratio (L1/L2) of an emission intensity (L1) observed in the range of 1.6 to 1.9 eV to an emission intensity (L2) observed in the range of 3.0 to 3.2 eV which corresponds to the band-to-band transition is preferably used as the index of evaluation of the stress stability. A peak intensity ratio (P1/P2) of a peak intensity (P1) of the emission intensity L1 to a peak intensity (P2) of the emission intensity L2 is more preferably used as the index of evaluation of the stress stability. It becomes thus possible to evaluate the stress stability of the oxide semiconductor thin film with increased accuracy.

Background of the present invention is briefly explained in the following.

After a great deal of consideration for the purpose of achieving the object, the present inventors have found that the emission intensity (preferably the peak intensity) of luminescence emitted from an oxide semiconductor thin film by irradiating the excitation light or an electron beam is a useful index for evaluating the stress stability of the oxide semiconductor thin film ($\Delta V_{th}$). Specifically, it was found that among the luminescence light emitted from the oxide semiconductor thin film, the emission intensity L1 (preferably peak intensity P1) observed in the particular range of 1.6 to 1.9 eV basically has a good correlation with the $\Delta V_{th}$. Small $\Delta V_{th}$ indicates excellent stress stability. As That is, it was found that L1 (or P1) tends to be decreased as $\Delta V_{th}$ becomes smaller.

On the other hand, it was also found that just using the emission intensity of the luminescence as described above [the emission intensity L1 (or the peak intensity P1) observed in the specific range of 1.6 to 1.9 eV L1] is not sufficient to correctly evaluate the stress stability in practice. This is considered due to a characteristic of the luminescence which is the subject of evaluation in the present invention is liable to be affected by factors other than a radiative level such as, for example, a non-radiative level in a semiconductor thin film, The radiative level is the cause of the stress stability. As a result of further studies then, it was found that the stress stability can be evaluated with higher accuracy by using the intensity ratio of the energies corresponding to each luminescence generated across a plurality of energy levels.

Specifically, exemplified as the intensity ratio are; L1/Q2 (or P1/Q3) wherein L1 (or P1) as mentioned above; and Q2 and Q3 are emission intensity and peak intensity, respectively, observed at a point of analysis other than the L1 (or P1), where the spectral shape in the range of in the analysis point matches (the spectrum overlaps) to the L1 (or P1).

Preferably used as the intensity ratio is the emission intensity ratio L1/L2 which is a ratio of L1 as described above to the emission intensity L2 observed in the range of 3.0 to 3.2 eV corresponding to the band-to-band transition. More preferably used is P1/P2 which is a ratio of the above-described P1 to the peak intensity P2 of the emission intensity L2. As explained in Examples described below, the intensity ratio has a very good correlation with the actual stress stability ($\Delta V_{th}$). It was found that the stress stability of the oxide semiconductor thin films can be evaluated with higher accuracy by using the intensity ratio as the evaluation standard.

The following is the reason to utilize the emission intensity L2 or peak intensity P2 as the standard, which is observed in the range of 3.0 to 3.2 eV and corresponding to band-to-band transitions. Since the light emission in the range is based on the band structure, the light emission intensity of the range has a correlation with the film quality of the semiconductor itself. In a case where the light emission intensity L1 or the peak intensity P1 described above is calculated low, it is not clear whether it is due to poor quality of the oxide semiconductor thin film or it is due to actually low light emission or low peak intensity independent of the quality of the oxide semiconductor thin film. However, by adopting the intensity ratio normalized by the L2 or P2, the cause becomes clear and the reliability of the display device can be evaluated correctly.

The evaluation method of the present invention includes; the method of evaluating the stress stability of an oxide semiconductor thin film on the basis of measured light emission intensity of luminescent light emitted by radiating excitation light at the specimen (the first embodiment); and the method of evaluating the stress stability of an oxide semiconductor thin film on the basis of measured light emission intensity of cathodoluminescence emitted by radiating an electron beam at the specimen (the second embodiment). The stress stability of the oxide semiconductor thin film is evaluated on the basis of the light emission intensity (L1) observed in the range of 1.6 to 1.9 eV of the luminescent light emitted from the oxide semiconductor thin film. They are different in that the first embodiment uses excitation light while the second embodiment uses an electron beam. However, both of the embodiments evaluates the stress stability of an oxide semiconductor thin film on the basis of light emission intensity of luminescence light and shares a common light emission mechanism.

The present invention uses in particular the emission intensity (or the peak intensity) observed in the predetermined range of energy as the index of the stress stability as repeatedly described. For example, "the emission intensity observed in the range of 1.6 to 1.9 eV (L1)" in the present specification means the emission intensity observed in the energy range. A mean value of the emission intensity in the above range and an area calculated by estimating the value and the spectral shape (the shape of the peaks) are included. On the other hand, "the peak intensity observed in the range of 1.6 to 1.9 eV (P1)" in the present specification means the maximum value of the emission intensity observed in the energy range. Although depending on the shape of the emission spectrum there may be a case in which a clear peak cannot be obtained, it is possible to determine the position by an energy level or the like even in such a case.

Among the parameters, it is recommended to use the luminescence intensity such as the mean value and the area calculated by estimating the spectral shape of the emission as an index from the following viewpoints. Peaks observed in the emission spectrum in the present invention often have a broad shape which usually indicates that defects derived from the same cause are dispersed by fluctuations of the structure. When the degree of the fluctuation is different, even emission peaks having the same peak intensity may have a different width in the emission spectrum (half maximum full width). Therefore, there could be a possibility to estimate the amount of the defects in an incorrect manner when using the peak intensity as the index. Considering this problem, it is correct from the point of view in physics to use the area calculated by estimating the spectral shape (the shape of the peak) as described above. On the other hand, in the sense of ease of the measurement, it is recommended to use the peak intensity as the index. This is because the spectral shapes show little variations in the oxide semiconductor of interest according to a study to date by the present inventors.

The same holds for "the light emission intensity (L2) which is observed in the range of 3.0 to 3.2 eV" and "the peak intensity (P2) observed in the range of 3.0 to 3.2 eV" in the present specification.

The "emission intensity L2 observed in the range of 3.0 to 3.2 eV corresponding to the band-to-band transition" which is used to calculate the intensity ratio, is essentially the entire emission intensity observed in the range corresponding to the band-to-band transition. As long as it satisfies the requirements, the emission intensity of the spectrum observed in the vicinity of 3.1 eV may be adopted as L2. Also, an emission intensity slightly out of the specified range of "3.0 to 3.2 eV" (for example, those within a range from about 2.5 to 3.5 eV) may also be included within the scope of the present invention as long as it satisfies the requirements.

Using the indexes, the method to evaluate stress stability of an oxide semiconductor thin film is explained in detail in the following.

First, a specimen having an oxide semiconductor thin film is prepared.

An amorphous oxide semiconductor comprising one or more kinds of element selected from a group consisting of In, Ga, Zn, and Sn is preferably used for the oxide semiconductor thin film. These elements may be contained alone, or two or more kinds thereof may be used in combination. Specifically, examples of the semiconductor include oxides such as In oxide, In—Sn oxide, In—Zn oxide, In—Sn—Zn oxide, In—Ga oxide, Zn—Ga oxide, In—Ga—Zn oxide, and Zn oxide. The oxide semiconductor thin film may contain an element other than these elements and oxygen. Such an element is, for example, Mn or the like.

Thickness of the oxide semiconductor thin film is preferably, for example, 20 to 100 nm, and more preferably 40 to 50 nm.

The specimens to be used in the present invention is comprising an oxide semiconductor thin film on a substrate. Various kinds of substrates usually used in the technological field of the present invention may be adopted for the substrate. For example, glass substrates for liquid crystal display devices having a thickness of about 0.7 mm and a size (an area) of several tens of square centimeters to more than a few square meters called the first generation to the tenth generation may be used.

The oxide semiconductor thin film may be formed directly on a substrate in the specimens. Alternatively, the specimens may have the oxide semiconductor thin film on top of a metal film formed on a substrate. The accuracy is improved in the latter type of the specimens since luminescence from a glass substrate induced by irradiation of excitation light or electron beam may be avoided.

The excitation light or the electron beam is irradiated to the specimen. If the oxide semiconductor thin film contains a defect which deteriorates the stress stability, the emission intensity due to the defect is obtained. It is preferable to set the irradiation condition of the excitation light or the electron beams to be suitable for respective composition and thickness of the oxide semiconductor thin film, specifically as follows. When using an electron beam, for example, the acceleration voltage is preferably set to about 5 kV, and more preferably about 2 kV. Electrons accelerated at an acceleration voltage of about 2 kV penetrate into a semiconductor by approximately 40 nm. Because thickness of the widely-used semiconductor film is about 30 to 50 nm, it is possible to evaluate the entire semiconductor film. On the other hand, for the excitation light it is recommended to use a radiation having energy larger than the bandgap (3.2 eV). A UV semiconductor laser of another type, a UV-LED, a Hg—Cd laser or the like are preferably used.

Subsequently, the emitted luminescence light and the emission intensity are measured. Specifically, when the specimen is subjected to irradiation of an excitation light, the photoluminescence light induced by the excitation light is measured, whereas when the specimen is irradiated by an electron beam, cathodoluminescence excited by the electron beam is measured. The luminescence is preferably measured at room temperature with an acceleration voltage 2 kV, for example.

To execute the evaluation method of the present invention, it is recommended to use a measurement device comprising; an irradiation device for irradiating the excitation light or an electron beam to the measurement portion of the specimen, a light emission device for measuring light emission generated by the irradiation of the excitation light or the electron beam at the defects in the oxide semiconductor thin film. The measurement device preferably comprises a processing device that is able to measure the entire spectrum over the visible light region and has a function to extract the peak intensity observed in the range from 1.6 to 1.9 eV of the spectrum. It is also possible to use the measurement device in combination of a light detection mean such as a CCD (charge-coupled device), a photomultiplier tube, and a photodetector element, and a filter which selectively transmits only light having energy from 1.6 to 1.9 eV.

The processing unit (apparatus for extracting the peak intensity or the like) preferably has a computer and a stage controller. Among them, the computer comprises a CPU (Central Processing Unit), a storage unit, and an interface for input and output signals, having a function of performing various processes by the CPU executing a predetermined program. For example, the computer outputs a timing signal representing the output timing of the excitation light to the pulsed laser and the processing device, records the spectral intensity values of the output by the detection means in a storage unit in the computer, and calculates the peak intensity from a broad peak present in the range of 1.6 to 1.9 eV. The stage controller has a function of performing positioning control of the measurement portion in the oxide semiconductor thin film specimen by controlling an X-Y stage in accordance to the instruction from the computer.

Specifically, the evaluation method using the excitation light as a mean for excitation and utilizing photoluminescence as in the first embodiment preferably uses a measurement device comprising a laser light source for excitation and a device for measuring the luminescence generated by the irradiation of the excitation light at the defects in the oxide semiconductor thin film. The aforementioned measurement device is preferably equipped with a spectrometer that is able to measure the entire spectrum over the visible light region, having a function to extract the peak intensity observed in the range from 1.6 to 1.9 eV from the spectrum. The measurement device may also be used in combination of a light detection mean such as a CCD, a photomultiplier tube, and a photodetector element, and a filter which selectively transmits only light having energy from 1.6 to 1.9 eV. The optical path is preferably equipped with a mirror and the condenser lens by which the emitted luminescence light can be efficiently collected.

For the laser light source for excitation used in the first embodiment, a light source such as pulse laser light from a semiconductor laser which emits pulsed ultraviolet radiation (YLF laser third harmonic or the like) as the excitation light having, for example, a wavelength of 349 nm, power (pulse energy) of 1 µJ/pulse, a pulse width of about 15 ns, and a beam diameter of about 1.5 mm. Penetration length in the wavelength (the wavelength of ultraviolet light) is about 200 nm that is comparable with a thickness of the oxide semiconductor thin film specimen (100 nm) of Examples.

The excitation light emitted from the pulse laser may be any radiation having energy about the same as or larger than the bandgap of the oxide semiconductor thin film specimen. In addition to the above-described YLF laser third harmonic pulse laser, a He—Cd laser, an argon ion laser, or the like may also be used as the laser light source capable of irradiating continuous light. It is essential here for the excitation light to have energy equal to or larger than the bandgap of the oxide semiconductor thin film specimen for the formation of electron-hole pairs which generate the luminescence light in the specimen.

The luminescence light (photoluminescence light in the first embodiment) which is emitted from the specimen is reflected and focused by the mirror to reach a detector. A mirror having an elliptical surface is preferably used since the luminescence light can be condensed at the focal point. The entrance of the optical fiber is installed at the focal point. The emitted luminescence light is guided to a spectroscope to be decomposed depending on respective wavelength. The emission intensity of each spectrum is then recorded.

On the other hand, in the evaluation method utilizing an electron beam as the excitation source and the cathodoluminescence as in the second embodiment, electrons emitted from the electron gun disposed in vacuum are focused and irradiated to a specimen. When using an electron beam, it is possible to use a conventional scanning electron microscope having a high spatial resolution. High performance of the evaluation is thus expected as compared to the first embodiment in which excitation light is used.

The evaluation method for an oxide semiconductor thin film according to the present invention is described in detail hereinabove.

The present invention includes a quality control method for an oxide semiconductor thin film by applying the evaluation method to any of manufacturing processes after an oxide semiconductor thin film is formed on a substrate. By applying the evaluation method to any of the manufacturing processes, it becomes possible to feedback the results of evaluation of electrical properties (stress stability) of the oxide semiconductor thin film and to control the film quality by way of adjusting the manufacturing conditions. Quality control of the oxide semiconductor can be appropriately conducted, accordingly.

Here, the "any of manufacturing processes" means any process after the formation of the oxide semiconductor thin film on a substrate. Specifically, the evaluation method may be performed immediately after forming the oxide semiconductor thin film. Alternatively, the evaluation method may be performed for an oxide semiconductor film formed on a substrate or on a gate insulator film after a heat treatment (pre-annealing treatment) in, for example, an oxygen or water vapor atmosphere. Further alternatively, the evaluation method may be performed before the formation of a passivation film (passivation insulator film). Moreover, the evaluation method may be performed in a single processing step or more than one processing steps in the course of manufacturing. By adopting the evaluation method of the present invention in more than one process as in the latter case, in-plane distribution of an oxide semiconductor thin film (in-plane variation of $V_{th}$) can be evaluated by scanning the entire substrate.

The pre-annealing treatment is a heat treatment method used to improve the film quality of oxide semiconductor thin film. The preferred pre-annealing conditions may differ depending on composition and manufacturing conditions of the oxide semiconductor thin film. It may be appropriately configured. for example, at atmospheric pressure in an air or water vapor-containing, or 100% oxygen ambient; at a temperature of about 250° C. or higher and 400° C. or lower; for a period of about 10 minutes to 3 hours. From the preferred pre-annealing conditions described above, a pre-annealing condition that can improve the stress stability may be selected by using the evaluation method of the present invention.

Hereinbelow, the embodiments of the quality control method of an oxide semiconductor thin film according to the present invention are described further in detail referring to the figures.

The quality control method for the oxide semiconductor thin film comprises; (A) a process of irradiating an electron beam to the oxide semiconductor thin film and measuring a fluorescence spectrum induced by the irradiation, and (B) a process of evaluating the film based on the fluorescent spectrum.

The thickness of the oxide semiconductor thin film is not particularly limited. It may be, for example, 10 nm or larger and 500 nm or smaller.

The oxide semiconductor thin film may be formed on a surface of a substrate such as a glass or the like. As described below, each of as-deposited layers constituting a TFT may be used for the purpose of conducting measurement at every fabrication process of the TFT.

Irradiation of the electron beam and acquisition of luminescence spectrum induced by the irradiation may be carried out by using a generally-known cathodoluminescence measurement apparatus. Specifically, electron beam may by irradiated by using an electron gun or others. Luminescence spectrum may be detected (acquired) by a CCD (charge-coupled device) or a PMT (photo-multiplier tube) or the like.

According to the quality control method, it becomes possible to conduct a measurement in a microscopic portion using a cathodoluminescence measurement apparatus. Further, since the electron energy is large, it becomes applicable to a wide bandgap semiconductor (oxide) thin film for which a direct photoexcitation is difficult to induce.

(B) Process

A thin film is evaluated based on a fluorescence spectrum acquired by the cathodoluminescence in the (B) process. Ratio of intensities (I) of energy X (wavelength) corresponding to respective fluorescence generated between multiple energy levels are used for the evaluation criteria.

Figure 1:
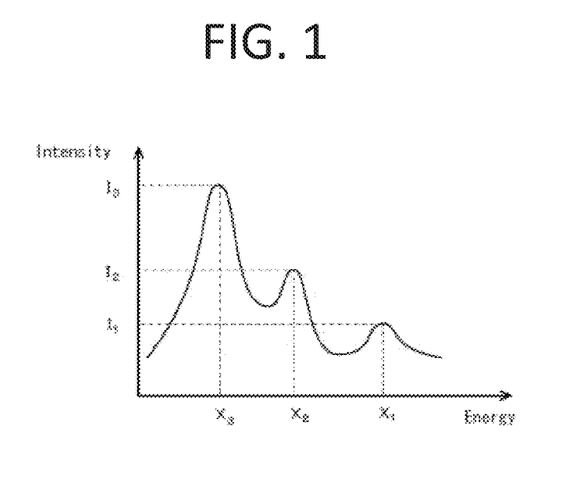
FIG. 1 is a schematic illustrating a fluorescence spectrum measured in the quality control method of the present invention.

The intensity I is preferably represented by the maximum value (peak) in a luminescence spectrum plotted in FIG. 1 representing energy X (wavelength) on the horizontal axis and intensity I on the vertical axis. Using a maximum value facilitates identifying the intensity and conducting the evaluation and control in an efficient manner. When a maximum value (peak) is not distinctive, the position may be determined by the energy levels or the like.

The quality control method performs a cathodoluminescence measurement for the oxide semiconductor thin film ((A) process), and an evaluation of the oxide semiconductor thin film using the intensity ratio of the fluorescence spectra ((B) process). It is thus possible to perform the measurement and evaluation at each manufacturing process even before completion of fabricating a transistor.

An intensity ratio $I_m/I_1$ is preferably used in the intensity of the energy wherein $I_1$ is intensity of an energy X corresponding to fluorescence generated between the conduction band and the valence band, and $I_2, I_3, \ldots I_m$ are intensities of one or more of the energy $X_2, X_3, \ldots X_m$ corresponding to fluorescence generated between the other energy levels (where m is an integer of 2 or larger).

Figure 2:
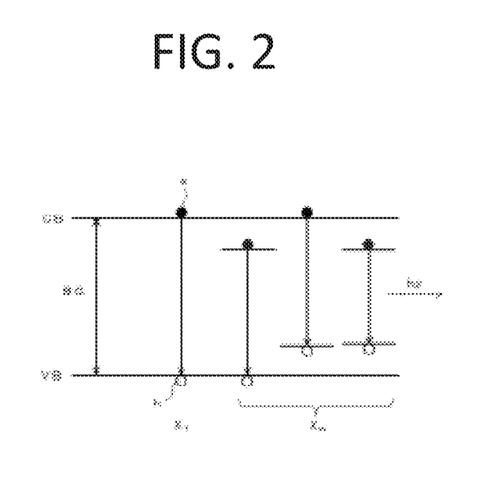
FIG. 2 is a schematic diagram illustrating a bandgap or the like in an oxide semiconductor thin film which is a subject of the quality control method of the present invention.

In order to explain the theory, firstly the principle of cathodoluminescence measurement is hereby described in reference to FIG. 2. A portion of the incident electrons in the oxide semiconductor thin film specimen is consumed to excite electrons residing in the valence band (VB) and acceptor levels to the conduction band (CB) and donor levels. As a result, electron ($e^-$)-hole (h) pairs are generated. The electron-hole pairs recombine by way of band-to-band (BG), donor levels, an acceptor levels, and defect levels, generating fluorescence as illustrated in FIG. 2.

Penetration depth (Re) of electron beam to a specimen can be determined by using an expression described below.

$$Re=27.6AE^{1.67}/Z^{0.9}\rho_m \qquad \text{(Expression 1)}$$

Here, Z is the atomic number, A is the atomic weight, E is the energy of the incident electrons, and $\rho_m$ is the density of the specimen. That is, it is possible to vary the penetration depth of the electrons by the acceleration voltage of the incident beam. For example, in case the oxide semiconductor thin film is an IGZO having a density of 6.3 g/cm$^3$, the penetration depth is 442 nm at an accelerating voltage 8 kV, 202 nm at 5 kV, and 86 nm at 3 kV.

In "Kotaibuturi (Solid State Physics), Vol. 44, p. 621 (2009)", hereinafter referred to Non-patent document 1, there are descriptions on the bandgap (BG) of IGZO film, and defect levels in the vicinities of the conduction band (CB) and the valence band (VB), and each of the defect density. It has been considered difficult to quantitatively measure the defect density. Therefore, evaluated using the intensity of the fluorescence spectrum in the present invention is the quality of semiconductor, the state of presence of defect levels or the like formed in the bandgap.

According to descriptions in the non-patent document 1, energies of each fluorescence in IGZO are;
the energy $X_1$ corresponding to the fluorescence generated across the conduction band and the valence band (bandgap: BG) is about 3.3 eV±0.2 eV, and
the energies $X_2$ and $X_3$ corresponding to fluorescence generated across other energy levels are about 2.5 eV±0.3 eV and about 1.9 eV±0.3 eV, respectively.

Stress stability and other quality of oxide semiconductor thin films such as IGZO can be easily controlled and evaluated by using the intensity ratio of these energies, accordingly. The intensity ratio is considered to represent the state of occurrence (presence) of defect levels and their densities, which leads to deterioration in terms of quality such as the stress stability of the TFT. On the other hand, intensity of the fluorescence is determined depending on the density of such defect levels. By monitoring intensity of the fluorescence generated across energy levels in reference to the intensity of fluorescence ($I_1$) corresponding to the bandgap for example, it is possible to confirm occurrence of a defect level or the like generated in the oxide semiconductor thin film and to control the quality by monitoring the value.

In particular, the intensity ratio $I_m/I_1$ is based on the intensity of the energy corresponding to the bandgap between the conduction band and the valence band. It is considered that the intensity ratio is correlated with status of each of the energy states formed in the oxide semiconductor thin film. It is thus possible to perform an evaluation with higher accuracy by using this intensity ratio.

For the intensity ratio $I_m/I_1$, a ratio of just a single pair such as for example, $I_2/I_1$, or, ratios of plurality of sets such as $I_2/I_1$ and $I_3/I_1$ may be used. As for the evaluation criteria, it may be specified so that the intensity ratio is within a predetermined range. Alternatively, only an upper or a lower limit may be specified. The lower or upper limit may be appropriately set according to properties such as band gap, the acceptor level, and the donor level of the oxide semiconductor thin film to be evaluated.

A ratio other than $I_m/I_1$, for example $I_3/I_2$ or the like in which the denominator is not $I_1$ may also be used as the intensity ratio.

It is preferable to perform the quality control method at the right time in the course of the each manufacturing process of the TFTs. Specifically, in manufacturing a thin film transistor comprising;

(X) a process of forming an oxide semiconductor thin film,
(Y) a process of annealing the oxide semiconductor thin film, and
(Z) a process of forming a passivation film on a surface of the oxide semiconductor thin film, the (A) and (B) processes are to be performed after each of the (X), (Y) and (Z) processes.

In the production of TFTs, conditions of depositing an oxide semiconductor thin film and its heat treatment as well as deposition of a passivation film on a surface of the oxide semiconductor thin film have a large influence on the quality of the oxide semiconductor thin film. It becomes thus possible to execute quality control in an efficient manner in the course of the manufacturing process by performing the measurement and evaluation after each of the processes (X) to (Z).

When the (A) process and the (B) process are performed after each of the (X) to (Z) processes and the oxide semiconductor thin film includes In, Ga, Zn, and O, and
the fluorescent energy $X_1$ is 3.3 eV±0.2 eV,
the fluorescent energy $X_2$ is 2.5 eV±0.3 eV, and
the fluorescent energy $X_3$ is 1.9 eV±0.3 eV, the criteria are preferably specified to;
an intensity ratio $I_2/I_1$ is equal to or larger than 2.0 and equal to or smaller than 15.0, and/or an intensity ratio $I_3/I_1$ is equal to or larger than 3.0 and equal to or smaller than 30.0, after the (X) process,
an intensity ratio $I_2/I_1$ is equal to or larger than 5.0 and equal to or smaller than 30.0, and/or an intensity ratio $I_3/I_1$ is equal to or larger than 15.0 and equal to or smaller than 80.0, after the (Y) process, and
an intensity ratio $I_2/I_1$ is equal to or larger than 6.0 and equal to or smaller than 20.0, and/or an intensity ratio $I_3/I_1$ is equal to or larger than 25.0 and equal to or smaller than 70.0, after the (Z) process.

Further, both $I_2/I_1$ and $I_3/I_1$ are preferably within each of the range.

The criteria are more preferably specified to;
an intensity ratio $I_2/I_1$ is equal to or larger than 2.0 and equal to or smaller than 8.0, and/or an intensity ratio $I_3/I_1$ is equal to or larger than 3.0 and equal to or smaller than 20.0, after the (X) process, an intensity ratio $I_2/I_1$ is equal to or larger than 5.0 and equal to or smaller than 15.0, and/or an intensity ratio $I_3/I_1$ is equal to or larger than 15.0 and equal to or smaller than 50.0, after the (Y) process, and
an intensity ratio $I_2/I_1$ is equal to or larger than 6.0 and equal to or smaller than 10.0, and/or an intensity ratio $I_3/I_1$ is equal to or larger than 25.0 and equal to or smaller than 40.0, after the (Z) process.

By specifically adopting the criteria in each process of manufacturing IGZO thin films, it is possible to perform better quality control.

When performing the (A) process after each of the (X) to (Z) processes, an oxide semiconductor thin film is usually deposited on a surface of the gate insulator film. Further, the passivation film is formed on a surface of the oxide semiconductor thin film when performing the (A) process after the (Z) process. By performing the measurement and evaluation for such deposited thin films, the quality control for each production process is facilitated.

The TFT may be fabricated by a generally-known method. Specifically, the TFT 1 illustrated in FIG. 3 can be obtained, for example, by;
a process of depositing a film as a gate electrode 3 on a surface of a substrate 2,
a process of patterning the film to form the gate electrode 3,
a process of forming a gate insulator film 4 that covers the gate electrode 3,
a process of depositing an oxide semiconductor thin film 5 on a surface of the gate insulator film 4 ((X) process),
a process of annealing the oxide semiconductor thin film 5 ((Y) process),
a process of forming a passivation film 6 on a surface of the annealed oxide semiconductor thin film 5 ((Z) process),
a process of patterning the passivation film 6,
a process of depositing a film which is to be a source electrode 7 or a drain electrode 8,
a process of patterning the film to form the source electrode 7 and the drain electrode 8,
a process of forming a passivation film 9 disposed at the outermost surface,
a process of forming a contact hole 10, and
a process of annealing the whole again.

The films for respective electrode, passivation film, and the insulator film may be formed by generally-known methods such as for example a sputtering method and an evaporation method. The patterning and the formation of contact holes may be also carried out by generally-known methods such as for example photolithography and wet or dry etching.

Figure 3:
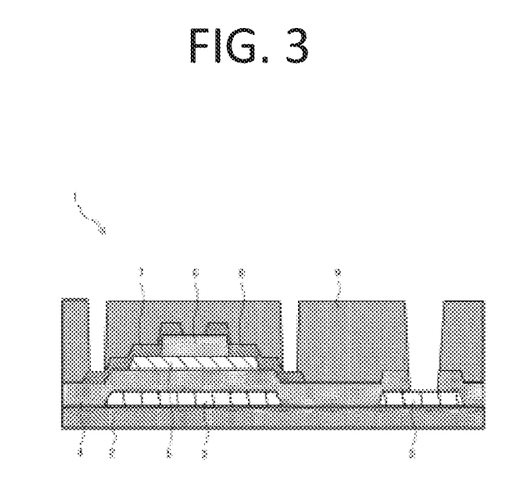
FIG. 3 is a schematic cross-sectional view of a TFT used in Example 1.

Deposition of the oxide semiconductor thin film 5, that is the (X) process, may be carried out by, for example, a sputtering method. The sputtering may preferably be carried out using a sputtering target with substrate temperature set to room temperature. Additive amount of oxygen may appropriately be controlled according to the configuration of a sputtering system and the composition of the target. The additive amount of oxygen may preferably be controlled by the addition of oxygen so that the carrier concentration in the oxide semiconductor thin film becomes approximately from $10^{15}$ to $10^{16}$ $cm^{-3}$.

The annealing (pre-annealing treatment) of (Y) process can improve the quality of the oxide semiconductor tin film 5. He annealing treatment may be performed for example in 100% oxygen atmosphere under atmospheric pressure. The treatment time is to be for example 10 minutes or longer and 3 hours or shorter. The treatment temperature is to be for example 300° C. or higher and 400° C. or lower.

As explained above, according to the quality control method of an oxide semiconductor thin film of the present invention, the direct measurement can be carried out for each manufacturing process of the thin film transistor. According to the quality control method it is possible to monitor each manufacturing process, to increase the yield of the TFT, and to realize an efficient production, accordingly.

EXAMPLES

The present invention is described hereinafter more specifically by way of examples, but the present invention is not limited to the following examples.

Fabrication Examples 1 to 4

TFTs are fabricated in the following procedure. In the course of the fabrication, they were measured and evaluated by the quality control method according to the present invention.

First, a Ti thin film of 100 nm in thickness was deposited as a gate electrode on a glass substrate ("EAGLE 2000" available from Corning Inc, having a diameter of 100 mm and a thickness of 0.7 mm). A gate electrode was then fabricated by patterning using a generally known method. The Ti thin film was deposited by DC sputtering method using a pure Ti sputtering target.

Next, a $SiO_2$ gate insulator film was formed. The gate insulator film was formed by a plasma CVD method under the conditions; carrier gas, a mixed gas of $SiH_4$ and $N_2O$; plasma power, 100 W; and deposition temperature, 300° C.

Then, the oxide semiconductor thin film was formed by a sputtering method ((X) process). The oxide semiconductor thin film was IGZO (In:Ga:Zn compositional ratio=1:1:1). The apparatus used in the sputtering was "CS-200" available from ULVAC, Inc., and the sputtering conditions were as follows:
(Sputtering Conditions)
 Substrate temperature: room temperature
 Gas pressure: 1 to 5 mTorr
 Oxygen partial pressure: $O_2/(Ar+O_2)=4\%$
 Film thickness: 50 to 150 nm After each oxide semiconductor layer was deposited in the manner described above, patterning was carried out by photolithography and wet etching. "ITO-07N" available from Kanto Chemical Co, Inc. was used as an acid-based wet etchant. It was confirmed in the present Example that all of the oxide semiconductor thin films subjected to the experimental were appropriately etched without forming etching residues.

After patterning the oxide semiconductor film, a pre-annealing treatment was conducted for the purpose of improving the quality of the film ((Y) process). The pre-annealing was carried out at 350° C. for 1 hour in 100% oxygen atmosphere or in air atmosphere.

Next, a passivation film (an etch stopper layer) is formed by a plasma CVD method ((Z) process), followed by patterning by a commonly known method.

Then a Ti thin film was deposited to a thickness of 100 nm by DC sputtering method using a pure Mo, followed by patterning. The deposition and patterning methods of the Ti thin film for the source-drain electrode was the same as for the gate electrode. The Ti film was subsequently subjected to ultrasonic cleaning in an acetone solution to remove unwanted photoresist. The length and width of the TFT channel were made 10 μm and 200 μm, respectively.

After the source-drain electrode was formed as described above, a passivation layer to protect an oxide semiconductor layer was formed thereon. A layered film having the total thickness of 400 nm consisting of $SiO_2$ having a thickness of 200 nm and SiN having a thickness of 200 nm was used as the passivation layer. The formation of the $SiO_2$ and SiN films described above was carried out by a plasma CVD method using "PD-220NL" available from SAMCO Inc. In this Example, after plasma treatment was carried out by $N_2O$ gas, the $SiO_2$ film and the SiN film were successively formed. A mixed gas of $N_2O$ and $SiH_4$ was used for the formation of the $SiO_2$ film, and a mixed gas of $SiH_4$, $N_2$ and $NH_3$ was used for the formation of the SiN film. In both cases, the film formation power was set to 100 W and the film formation temperature was set to 150° C.

Then, a contact hole to be used for probing to evaluate transistor characteristics was formed in the passivation layer by photolithography and dry etching.

A post-annealing treatment was carried out finally. The post-annealing was conducted in a 100% nitrogen atmosphere under atmospheric pressure at 250° C. for 1 hour. Each of the TFTs was thus completed.

As summarized in Table 1, 4 patterns of fabrication were carried out by varying gas pressure to form the oxide semiconductor, with or without the pre-annealing treatment, and with or without the passivation film (the etch stopper layer) to obtain fabrication examples 1 to 4.

For each of the TFTs thus obtained, (1) transistor characteristics [drain current ($I_d$)-gate voltage ($V_g$) characteristics] and (2) variations of the threshold voltage ($V_{th}$), SS value, and carrier mobility were evaluated before and after applying the stress as explained below.
(1) Measurement of Transistor Characteristics A semiconductor parameter analyzer "4156C" available from National Instruments was used for measuring the transistor characteristics. The detailed measurement conditions were as described below.
 Source voltage: 0 V
 Drain voltage: 10 V
 Gate voltage: −30 to 30 V (measurement increment: 1 V)
(2) Evaluation of Stress Stability (Light Irradiation while Applying Negative Bias as the Stress)

In the present example, stress application tests were carried out by light irradiation while applying negative bias to the gate electrode for simulation of environments (stress) at the time of actual panel drive. The stress application conditions were as described below. As the light source, white light was selected as it is used for backlight in display devices.
 Gate voltage: −20 V
 Substrate temperature: 60° C.
 Light stress:
 Light source: white LED ("LXHL-PW01" available from PHILIPS)
 Illuminance (intensity of light irradiated onto TFTs): 25,000 NIT
 Irradiation device: YSM-1410 available from Yang Electronic Systems Co., Ltd.
 Stress application time: 2 hours The threshold voltage is roughly a value of gate voltage ($V_g$) at the time when a transistor is shifted from off-state (state where drain current ($I_d$) is low) to on-state (state where drain current is high). In the present example, the voltage in the case where the drain current is about 1 nA between on-current and off-current is defined as the threshold voltage ($V_{th}$), and change (amount of shift) of the threshold voltage before and after applying the stress was measured.

SS value is a minimum value of a gate voltage needed to increase the drain current by one digit. Carrier mobility (field-effect mobility) was derived from a slope of $I_d \propto (V_g - V_{th})$ in a linear region where the relation of $I_d \propto (V_g - V_{th})$ holds.

Table 1 indicates threshold value shift for each of the transistor (specimens 1 to 4).

TABLE 1

| Specimen | | Gas pressure to form oxide semiconductor (mTorr) | Pre-annealing treatment | Passivation film (Etch stopper layer) | $\Delta V_{th}$ (V) |
|---|---|---|---|---|---|
| Fabrication example 1 | 1 | 5 | Conducted | Conducted | 20.75 |
| Fabrication example 2 | 2 | 1 | Not conducted | Conducted | 8.25 |
| Fabrication example 3 | 3 | 1 | Conducted | Not conducted | 13.25 |
| Fabrication example 4 | 4 | 1 | Conducted | Conducted | 3 |

Examples 1 to 4

In the course of fabrication of each of the TFTs, the cathodoluminescence measurements were conducted after (X) process, (Y) process, and (Z) process.

"MP-Micro-M-IRP" available from Horiba Ltd., was used for the measurement. An electron beam was irradiated by using an electron gun at an acceleration voltage of 5 kV. Induced fluorescence was detected by a CCD at an exposure time of 30 seconds.

Figure 4:
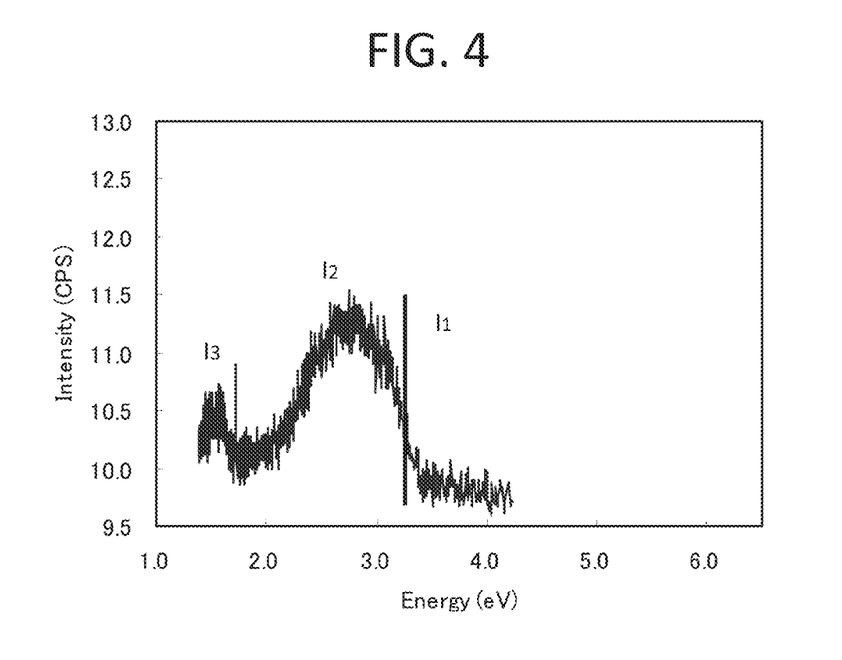
FIG. 4 is a spectral diagram of Example 1 (Sample 1).
Figure 5:
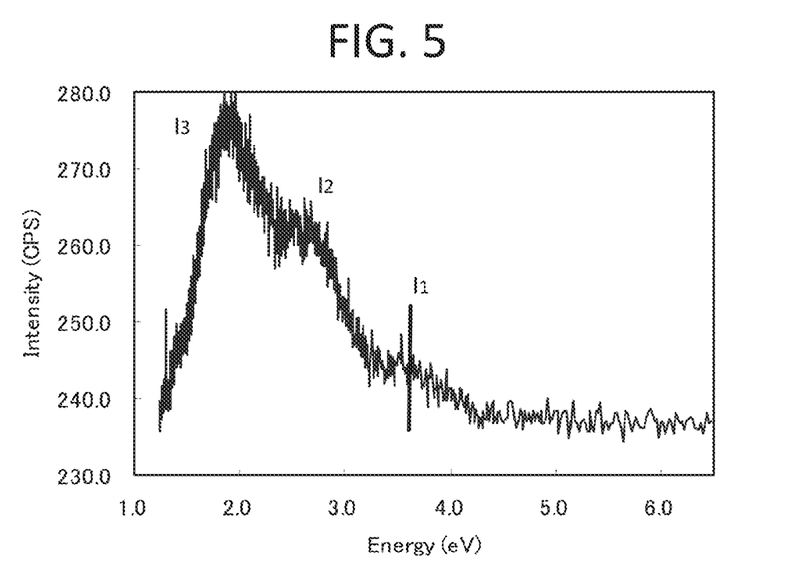
FIG. 5 is a spectral diagram of Example 2 (Sample 2).
Figure 6:
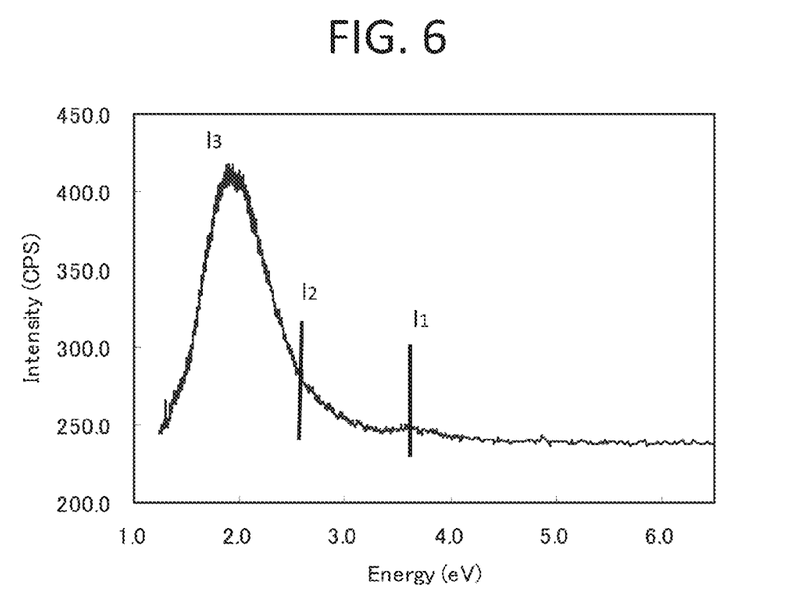
FIG. 6 is a spectral diagram of Example 3 (Sample 3).
Figure 7:
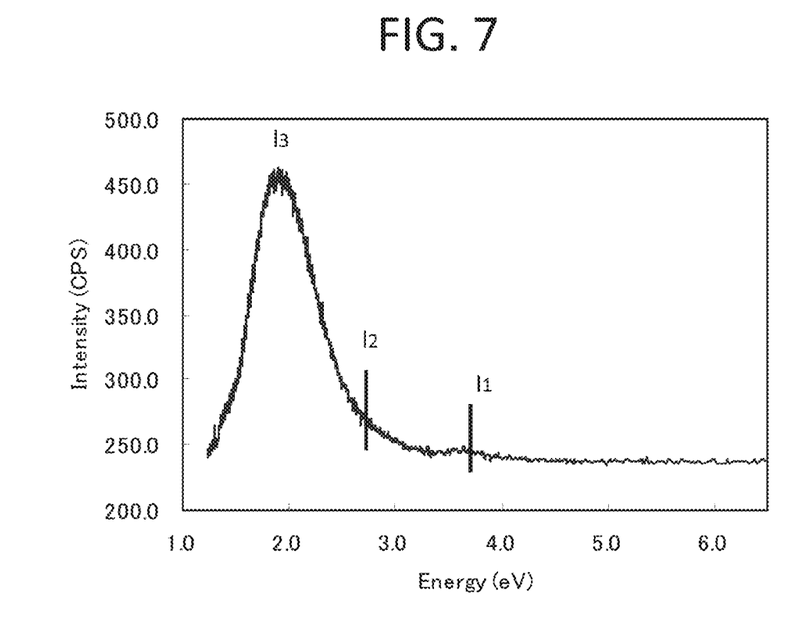
FIG. 7 is a spectral diagram of Example 4 (Sample 4).

Measurement results (spectral diagram) of Samples 1 to 4 described in Table 1 are presented in FIGS. 4 to 7, respectively. FIG. 4 (Sample 1) and FIG. 5 (Sample 2) are spectra acquired after (X) process. FIG. 6 (Sample 3) is a spectrum acquired after (Y) process. FIG. 7 (Sample 4) is a spectrum acquired after (Z) process.

In each of the oxide (IGZO) thin films, three peaks ($I_1$ to $I_3$) were observed. Respective value is indicated in Table 2.

bad in the judgments after the pre-annealing and the formation of the etch stopper layer, respectively. Specimen 4, on the other hand, was evaluated good in all the judgments, showing small threshold value shift.

It was thus elucidated that the intensity ratio of the cathodoluminescence spectra and the threshold voltage shift are correlated with each other, which can be appropriately used for the quality control.

Example 5

In the following example, the evaluation method of the second embodiment using cathodoluminescence in which an electron beam was used for the excitation. As described above, the emission mechanism is the same as in the evaluation method of the first embodiment using photoluminescence which is induced by photoexcitation, and it is thus possible to obtain a similar result of evaluation to the present example.

(1) Preparation of Specimens

Firstly, an amorphous oxide semiconductor (InGaZnO) thin film specimen was prepared. Specifically, a Mo film was formed on a glass substrate ("EAGLE XG" available from Corning Incorporated, having a diameter of 4 inches) for the purpose of preventing light emission from the substrate by a DC sputtering method under the following conditions. After that, an oxide semiconductor thin film was deposited by a sputtering method. Detailed conditions were as described below.

(Deposition Condition of Mo Film)

The deposition was performed at room temperature with an input power of 300 W dc. Size of the pure Mo sputtering target was 4 inches. Gas pressure was 2 mTorr during the deposition. Thickness of the deposited Mo film was 100 nm.

(Deposition Conditions of Oxide Semiconductor Thin Film)

Composition of sputtering target: $InGaZnO_4$ (In:Ga:Zn=1:1:1 (in atomic ratio)

Substrate temperature: room temperature

Thickness of oxide semiconductor layer: 100 nm

Addition amount of oxygen: $O_2/(Ar+O_2)$=4%, 8% (in volume ratio)

TABLE 3

| | | | | | | | Evaluation | | |
|---|---|---|---|---|---|---|---|---|---|
| | Specimen | $I_1$ (CPS) | $I_2$ (CPS) | $I_3$ (CPS) | $I_2/I_1$ | $I_3/I_1$ | After deposition of oxide semiconductor | After pre-annealing | After formation of etch stopper layer |
| Example 1 | 1 | 1.1 | 1.5 | 0.7 | 1.3 | 0.6 | Bad | Bad | Bad |
| Example 2 | 2 | 7.5 | 25.2 | 38 | 3.3 | 5 | Good | Bad | Bad |
| Example 3 | 3 | 8.6 | 43.8 | 164.6 | 5.1 | 19.1 | Good | Good | Bad |
| Example 4 | 4 | 7.4 | 48.1 | 212.3 | 6.5 | 28.6 | Good | Good | Good |

By using the intensity ratios of $I_2/I_1$ and $I_3/I_1$, the specimens were evaluated by the criteria summarized in Table 3.

TABLE 3

| | After deposition of oxide semiconductor | After pre-annealing | After formation of etch stopper layer |
|---|---|---|---|
| $I_2/I_1$ | 2.0 or larger | 5.0 or larger | 6.0 or larger |
| $I_3/I_1$ | 3.0 or larger | 15.0 or larger | 25.0 or larger |

Specimen 1 was evaluated bad in the judgment after deposition of the oxide semiconductor as $I_2/I_1$ was 1.3 and $I_2/I_1$ was 0.6, in which the threshold value shift of the transistor was also large. Similarly, specimens 2 and 3 were evaluated Then, oxide semiconductor thin film specimens were prepared by conducting a pre-annealing treatment in a condition of atmospheric pressure in air at 350° C. for 60 minutes (2) Measurement of Cathodoluminescence of Each Sample For the specimens thus obtained, for the purpose of investigating the effect of stress stability due to the difference of the plasma damage on the same substrate plane, three specimens were prepared by being cut out from different locations on the same substrate plane [Specimen 1 (from the center portion of the substrate), Specimen 2 (upper side of Specimen 1), and Specimen 3 (lower side of Specimen 1), each having a size of 2 cm] to measure the cathodoluminescence spectrum in the following manner.

A cathodoluminescence measurement apparatus available from Horiba was used for the measurement. An electron beam was irradiated by using an electron gun at an acceleration voltage of 2 kV. Induced fluorescence was detected by a CCD at an exposure time of 60 seconds to obtain an emission spectrum in a visible light range.

Figure 8:
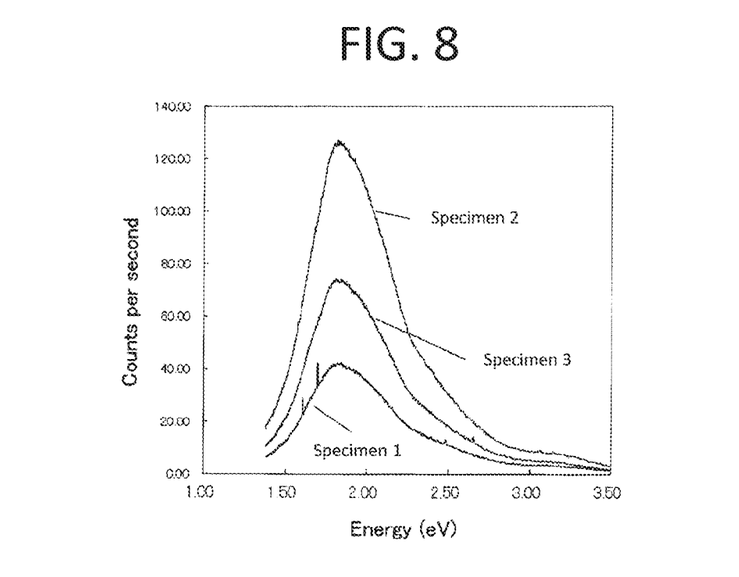
FIG. 8 is a graph illustrating changes in cathodoluminescence spectra of the samples 1 to 3 which were used in Example 5.

Detailed measurement conditions are as follows.
Observation equipment: Field emission scanning electron microscope (FE-SEM) S-4000 available from Hitachi, Ltd.
Acceleration voltage: 2 kV
Analyzer: MP-Micro-IRP available from Horiba, Ltd.
Diffraction grating: 300 lines/mm, Blaze 600 nm, wavelength resolution of 0.8 nm or more, 350 to 950 nm
Detector: CCD [DU420A-OE available from Andor Technology Ltd., 1024 Ch, 200 to 1100 nm]
Measurement temperature: RT Illustrated in FIG. 8 are the changes in the cathodoluminescence spectrum measured on the basis of the apparatus for each of the specimens described above. As illustrated in FIG. 8, each specimen has a broad peak intensity in the vicinity of approximately 1.8 eV. The peak intensity P1 of the specimen 1 was 41 CPS, the peak intensity P1 of the specimen 2 was 125 CPS, and the peak intensity P1 of the specimen 3 was 72 CPS. The peak intensity was large in the order of Specimen 2>Specimen 3>Specimen 1.

(3) Evaluation of Stress Stability ($\Delta V_{th}$)

(3-1) Preparation of TFT Specimen

For the purpose of investigating stress stability of the specimens, TFT specimens were fabricated as described below.

Firstly, Mo gate electrode of 100 nm in thickness and $SiO_2$ gate insulator film of 250 nm in thickness were formed on the glass substrate used for the fabrication of the specimens. Deposition conditions of these were as follows.

(Deposition Conditions of Mo Gate Electrode)

A Mon film was formed by using DC sputtering method. The deposition was conducted at room temperature with an input power of DC 300 W (size of the pure Mo sputtering target was 4 inches) and a gas pressure of 2 mTorr.

(Deposition Conditions of Gate Insulator Film)

A $SiO_2$ film was formed by using plasma CVD method. Specifically, the deposition was carried out with carrier gas: a gas mixture of $SiH_4$ and $N_2O$ ($N_2O$=100 sccm, $SiH_4/N_2$=40 sccm), deposition power: 300 W, and deposition temperature: 320° C.

After an oxide semiconductor layer of 40 nm in thickness was deposited on the gate insulator film under the same conditions as in "(1) preparation of a specimen" described above, patterning was carried out by wet etching. "ITO-07N" (a mixed solution of oxalic acid and water) available from Kanto Chemical Co., Inc., was used as a wet etchant. Immediately after patterning of the oxide semiconductor layer, a heat treatment (pre-annealing treatment) was carried out to improve the film quality. The pre-annealing conditions were the same as in "(1) preparation of a specimen" described above.

Then, an etch stopper layer (ESL) was formed at 230° C. by a CVD method on the surface of the oxide semiconductor thin film for the purpose of avoiding damages caused in subsequent processes. Then its patterning was performed. The ESL is a single layer structure of $SiO_2$ having a thickness of 100 nm. The pattering of the ESL was conducted by a photolithography and dry etching method. For the dry etching, reactive ion etching method was used. A gas mixture of $CHF_3$ and Ar was used for the etching.

Next, a Mo film was formed as a source-drain (S/D) electrode, followed by patterning. Deposition conditions for the Mo film were the same as for the Mo gate electrode except that thickness of the Mo film was made 200 nm.

A laminate film of $SiO_2$ and SiN was formed next as a passivation layer to protect the whole TFT by plasma enhanced CVD (PE-CVD) method. The deposition temperature was 150° C. Film thicknesses of $SiO_2$ and SiN were 100 nm and 150 nm, respectively. Then, a contact hole was formed by photolithography and dry etching method. The dry etching was reactive ion etching. Specifically, the $SiO_2$ was etched by using a gas mixture of $CHF_3$ and Ar whereas the SiN was etched by using a gas mixture of $SF_6$ and Ar to obtain the TFT specimens.

(3-2) Evaluation of Stress Stability (Light Irradiation while Applying Negative Bias as the Stress)

A stress test was carried out as follows and $I_d$-$V_g$ characteristics were investigated before and after applying the stress for each of the TFTs thus obtained. In the present Example, stress biasing test was carried out by applying negative bias onto the gate electrode while irradiating white light simulating a stress environment of actual liquid crystal display. The stress biasing conditions are as described below. A white LED is used for the light source simulating a back light for a liquid crystal display device.

Figure 9:
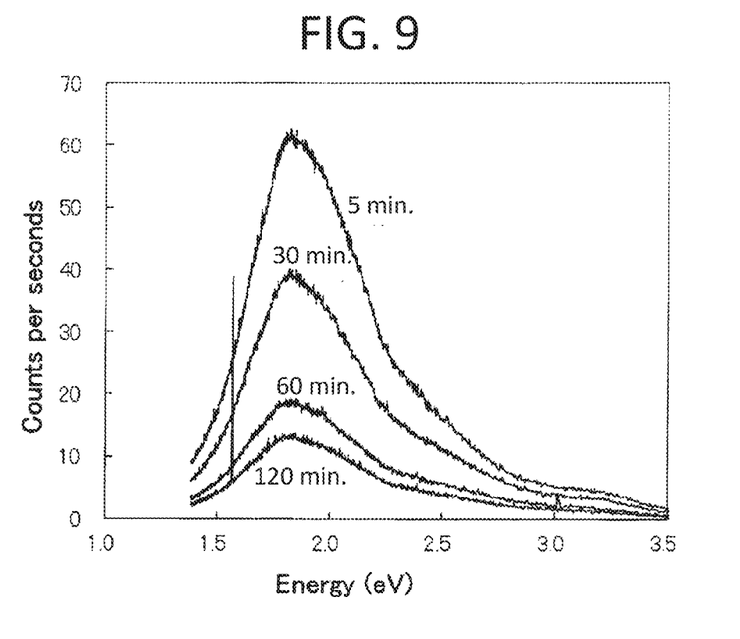
FIG. 9 is a graph illustrating changes in the cathodoluminescence spectra when the pre-annealing time was varied in a range of 5 to 120 minutes in Example 6.

Source voltage: 0V
Drain voltage: 10 V
Gate voltage: −20 V
Substrate temperature: 60° C.
Stress application time: 5, 30, 60, 120 minutes as indicated in FIG. 9
Light source: white LED (LXHL-PW01 available from PHILIPTS N.V.) 25000 nit For each of the specimens, $\Delta V_{th}$, the index of the stress stability, was calculated. $\Delta V_{th}$ is defined as an amount shift in the voltage in the case where the drain current is about 1 nA in between the on-current and the off-current states. $\Delta V_{th}$ of Specimen 1 was 0.5 V, $\Delta V_{th}$ of Specimen 2 was 2 V, and $\Delta V_{th}$ of Specimen 3 was 3.5 V. $\Delta V_{th}$ was large in the order of Specimen 3>Specimen 2>Specimen 1.

The smaller $\Delta V_{th}$ is, the more excellent in stress stability is as explained above. In the field of display devices, the criterion for acceptance in terms of the stress stability is generally $\Delta V_{th}$ of about 0.5V. When $\Delta V_{th}$ is about 0.5 V or smaller, the stress stability is good whereas the stress stability is often judged as bad when $\Delta V_{th}$ is greater than about 0.5 V.

From a comparison of the $\Delta V_{th}$ of each specimen with the above-described results in FIG. 8 (the peak intensity P1 of each specimen) based on the general criteria described above, it can be seen that both have a good correlation with each other. That is, Specimen 1 having the smallest $\Delta V_{th}$ as well as satisfying the evaluation criteria had the smallest peak intensity P1 among Specimens 1 to 3. On the contrary, Specimens 2 and 3 whose $\Delta V_{th}$ exceed the upper limit of the evaluation criteria had peak intensities larger than P1 of Specimen 1. It was thus found that the peak intensity P1 can be applied as an index that can determine the acceptability of the stress stability.

From the results described hereinabove, it was demonstrated that in-plane distribution of $\Delta V_{th}$ in different specimens having non-uniform plasma damages in a substrate can be evaluated with high accuracy by using the evaluation method according to the present invention.

Example 6

In the present example, pre-annealing time was varied for the specimens of Example 5 and their stress stabilities were evaluated.

Firstly, in the course of preparing specimen (1) of Example 5, pre-annealing treatments were carried out under various conditions described below to obtain specimens 1 to 4 as described below.

Specimen 1: pre-annealing conditions 1 (atmospheric pressure in air at 350° C. for 5 minutes)
Specimen 2: pre-annealing condition 2 (atmospheric pressure in air at 350° C. for 30 minutes)
Specimen 3: pre-annealing conditions 3 (atmospheric pressure in air at 350° C. for 60 minutes)
Specimen 4: pre-annealing conditions 4 (atmospheric pressure in air at 350° C. for 120 minutes)

For each of the specimens thus obtained, intensity P1 of a peak in respective cathodoluminescence spectrum in the vicinity of 1.8 eV was measured in the same manner as Example 5. Measuring portion was around the center of substrate for each specimen.

The results are summarized in FIG. 9.

Also, for each of Specimens 1 to 4, the peak intensity ratio (P1/P2) of the peak intensity P1 in the vicinity of about 1.8 eV to the peak intensity P2 in the vicinity of about 3.1 eV was calculated. The intensity ratios were 12 in Specimen 1, 11 in Specimen 2, 8 in Specimen 3, and 10 in Specimen 4. The intensity ratio was large in the order of Specimen 1 (pre-annealed for 5 minutes)>Specimen 2 (pre-annealed for 30 minutes)>Specimen 4 (pre-annealed for 120 minutes)>Specimen 3 (pre-annealed for 60 minutes).

On the other hand, TFT specimens were prepared and respective $\Delta V_{th}$ was calculated in the same manner as in Example 5. The $\Delta V_{th}$ were 3.75 V in Specimen 1 (pre-annealed for 5 minutes), 3.00 V in Specimen 2 (pre-annealed for 30 minutes), 1.25 V in Specimen 3 (pre-annealed for 60 minutes), and 3.00 V in Specimen 4 (pre-annealed for 120 minutes). The $\Delta V_{th}$ was large in the order of Specimen 1 (pre-annealed for 5 minutes)>Specimen 2 (pre-annealed for 30 minutes)=Specimen 4 (pre-annealed for 120 minutes)>Specimen 3 (pre-annealed for 60 minutes).

Figure 10:
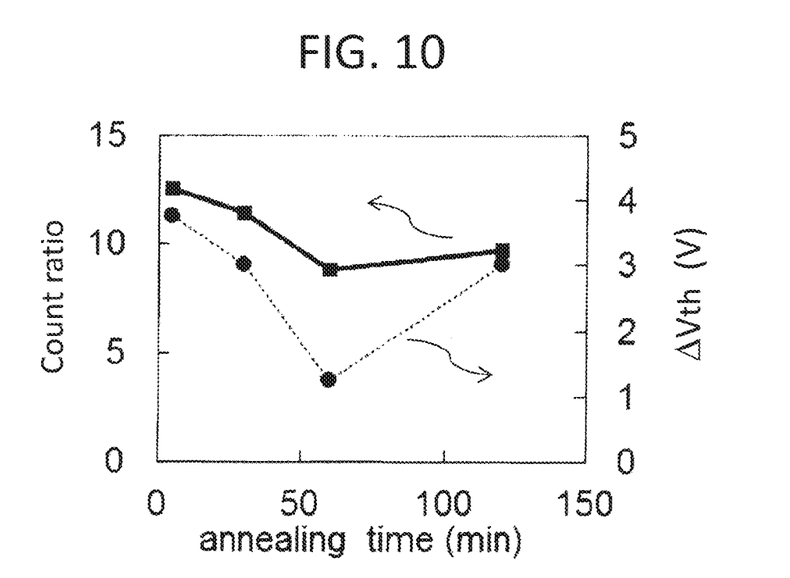
FIG. 10 is a graph illustrating the relationship between the peak intensity ratio (P1/P2) and the stress stability ($\Delta V_{th}$) at each annealing time in Example 6.

Relations between the pre-annealing time and peak intensity ratio (P1/P2) as well as the pre-annealing time and stress stability ($\Delta V_{th}$) are plotted in FIG. 10. In FIG. 10, the peak intensity ratio and the stress stability are indicated by filled square ■ and filled circle ●, respectively.

It was found in FIG. 10 that the intensity ratio (indicated by filled square ■ in the figure) and $\Delta V_{th}$ (indicated by filled circle ● in the figure) have an extremely fine correlation with each other. As the pre-annealing time got longer from 5 minutes (specimen 1) via 30 minutes (specimen 2) to 60 minutes (specimen 3), the peak intensity ratio and $\Delta V_{th}$ became smaller. In the meanwhile, the peak intensity ratio and $\Delta V_{th}$ increased when the pre-annealing time was 120 minutes as for the specimen 4.

It was thus found that the oxide semiconductor thin film of the present example can be accurately evaluated only by using the peak intensity ratio (P1/P2) without fabricating an actual TFT and that the highest stress stability is obtained by controlling the pre-annealing time to 60 minutes in the range of 5 to 120 minutes.

Following facts were found from results summarized in FIG. 9 (the peak intensity P1) and FIG. 10 (the peak intensity ratio P1/P2) regarding the specimen 4 for which the pre-annealing time was 120 minutes. When the heat treatment was performed for an extended period of time as for the specimen 4, structure of the entire thin film is disordered, resulting in significant decrease of the peak intensity P1 (see FIG. 9). It will then be concluded that specimen 4 is most superior in the stress stability as a consequence of judgment based solely on the peak intensity. However, it was confirmed that the stress stability is correctly evaluated by using the peak intensity ratio (P1/P2) in which the P1 is corrected by the peak intensity P2.

From the results explained above, it was demonstrated that the stress stability of oxide semiconductor thin films having different pre-annealing time can be evaluated with higher accuracy by using the peak intensity ratio (P1/P2) as the index.

The present application has been explained in detail by referring to specific embodiment in the above. It is obvious for a person skilled in the art that various modifications and corrections can be made within the scope and the spirit of the present invention. The present application claims the benefit of priority based on Japanese Patent Applications No. 2012-061258, No. 2013-004708, and No. 2013-055795 filed on Mar. 16, 2012, Jan. 15, 2013, and Mar. 18, 2013, respectively. The entire contents of the specification of the patent applications are incorporated herein by reference.

INDUSTRIAL APPLICABILITY

As explained hereinabove, the quality control method for an oxide semiconductor thin film of the present invention can be suitably used for quality control in manufacturing process of TFTs.

EXPLANATION OF REFERENCE NUMERALS

1 TFT
2 Substrate
3 Gate electrode
4 Gate insulator film
5 Oxide semiconductor thin film
5 Source-drain (S/D) electrode
6 Passivation film
7 Source electrode
8 Drain electrode
9 Passivation film
10 Contact hole

The invention claimed is:

1. A method for evaluating an oxide semiconductor thin film comprising evaluating the stress stability of an oxide semiconductor thin film on the basis of a light emission intensity of luminescent light excited when radiating an electron beam or excitation light at a sample at which the oxide semiconductor thin film is formed;
   wherein the stress stability of the oxide semiconductor thin film is evaluated on the basis of the light emission intensity (L1) observed in the range of 1.6-1.9 eV of the luminescent light excited from the oxide semiconductor thin film.

2. The method for evaluating an oxide semiconductor thin film according to claim 1;
   wherein the stress stability of the oxide semiconductor thin film is evaluated on the basis of peak intensity (P1) observed in the range of 1.6-1.9 eV.

3. The method for evaluating an oxide semiconductor thin film according to claim 1;
   wherein the stress stability of the oxide semiconductor thin film is evaluated on the basis of an intensity ratio of energies corresponding to each of the luminescent light generated across a plurality of energy levels of the oxide semiconductor thin film from which the luminescent light is excited.

4. The method for evaluating an oxide semiconductor thin film according to claim 3;
   wherein a ratio (L1/L2) of a light emission intensity (L1) observed in a range from 1.6 eV to 1.9 eV to a light emission intensity (L2) observed in a range from 3.0 eV to 3.2 eV corresponding to the band-to-band transition is used for the intensity ratio.

5. The method for evaluating an oxide semiconductor thin film according to claim 4;
   wherein a ratio (P1/P2) of a peak intensity (P1) observed in a range from 1.6 eV to 1.9 eV to a peak intensity (P2) observed in a range from 3.0 eV to 3.2 eV corresponding to the band-to-band transition is used for the intensity ratio.

6. The method for evaluating an oxide semiconductor thin film according to claim 1;
   wherein the oxide semiconductor thin film comprises one or more kinds of element selected from a group consisting of In, Ga, Zn, and Sn.

7. A quality control method for an oxide semiconductor thin film;
   wherein the evaluation method according to claim 1 is applied to any of manufacturing processes of the semiconductor after forming the oxide semiconductor thin film on a substrate.

8. The method for evaluating an oxide semiconductor thin film according to claim 2;
   wherein the stress stability of the oxide semiconductor thin film is evaluated on the basis of an intensity ratio of energies corresponding to each of the luminescent light generated across a plurality of energy levels of the oxide semiconductor thin film from which the luminescent light is excited.

9. The method for evaluating an oxide semiconductor thin film according to claim 8;
   wherein a ratio (L1/L2) of a light emission intensity (L1) observed in a range from 1.6 eV to 1.9 eV to a light emission intensity (L2) observed in a range from 3.0 eV to 3.2 eV corresponding to the band-to-band transition is used for the intensity ratio.

10. The method for evaluating an oxide semiconductor thin film according to claim 9;
    wherein a ratio (P1/P2) of a peak intensity (P1) observed in a range from 1.6 eV to 1.9 eV to a peak intensity (P2) observed in a range from 3.0 eV to 3.2 eV corresponding to the band-to-band transition is used for the intensity ratio.

11. The method for evaluating an oxide semiconductor thin film according to claim 2;
    wherein the oxide semiconductor thin film comprises one or more kinds of element selected from a group consisting of In, Ga, Zn, and Sn.

12. A quality control method for an oxide semiconductor thin film;
    wherein the evaluation method according to claim 2 is applied to any of manufacturing processes of the semiconductor after forming the oxide semiconductor thin film on a substrate.

* * * * *